(12) United States Patent
Kadomura et al.

(10) Patent No.: US 8,442,289 B2
(45) Date of Patent: May 14, 2013

(54) MEDICAL IMAGE PROCESSING DEVICE, METHOD FOR PROCESSING MEDICAL IMAGE AND PROGRAM

(75) Inventors: Takayuki Kadomura, Tokyo (JP); Taiga Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 303 days.

(21) Appl. No.: 12/937,447

(22) PCT Filed: Apr. 21, 2009

(86) PCT No.: PCT/JP2009/057902
§ 371 (c)(1),
(2), (4) Date: Oct. 12, 2010

(87) PCT Pub. No.: WO2009/131109
PCT Pub. Date: Oct. 29, 2009

(65) Prior Publication Data
US 2011/0033099 A1    Feb. 10, 2011

(30) Foreign Application Priority Data
Apr. 22, 2008 (JP) .................................. 2008-110918

(51) Int. Cl.
*G06K 9/00* (2006.01)
*G06K 9/34* (2006.01)

(52) U.S. Cl.
USPC ........................... 382/128; 382/132; 382/173

(58) Field of Classification Search .................. 382/128, 382/132, 173
See application file for complete search history.

(56) References Cited

U.S. PATENT DOCUMENTS

| | | | | |
|---|---|---|---|---|
| 6,198,797 B1 * | 3/2001 | Majima et al. | ................... | 378/98 |
| 7,054,406 B2 * | 5/2006 | Ikeda et al. | ....................... | 378/8 |
| 7,940,893 B2 * | 5/2011 | Krauss | ......................... | 378/98.9 |
| 8,077,828 B2 * | 12/2011 | Aoyama | ......................... | 378/62 |
| 2003/0152258 A1 * | 8/2003 | Jabri et al. | ..................... | 382/132 |
| 2006/0109953 A1 * | 5/2006 | Walter et al. | ....................... | 378/5 |
| 2007/0030944 A1 * | 2/2007 | Grasruck et al. | ................... | 378/4 |
| 2007/0092127 A1 * | 4/2007 | Grasruck et al. | ............. | 382/132 |
| 2007/0189443 A1 * | 8/2007 | Walter et al. | ....................... | 378/4 |
| 2008/0013672 A1 * | 1/2008 | Krauss et al. | ....................... | 378/4 |
| 2009/0147919 A1 * | 6/2009 | Goto et al. | ........................ | 378/86 |

FOREIGN PATENT DOCUMENTS

| | | |
|---|---|---|
| JP | 2007-111526 | 5/2007 |
| JP | 2007-268273 | 10/2007 |

OTHER PUBLICATIONS

International Search Report in PCT/JP2009/057902, Oct. 22, 2010.

* cited by examiner

*Primary Examiner* — Bhavesh Mehta
*Assistant Examiner* — Utpal Shah
(74) *Attorney, Agent, or Firm* — Cooper & Dunham LLP

(57) ABSTRACT

There is provided a medical image processing device that enables high-precision identification of the type of a biomedical tissue and display of an identification degree with respect to medical image information in multi-energy imaging. The medical image processing device acquires tissue information (statistic amount information such as average CT value, standard deviation of CT values, etc., display color, etc.) of a biomedical tissue every energy intensity of the multi-energy imaging. The medical image processing device creates an identification map for identifying the type of the biomedical tissue on the basis of the statistic amount information, and further creates an identification probability map for determining the identification degree of the biomedical tissue on the basis of the statistic amount information and the identification map. The medical image processing device acquires imaging information based on the multi-energy imaging, identifies the type of the biomedical tissue on the basis of the identification map, determines the identification degree on the basis of the identification probability map and displays in accordance with the identification.

8 Claims, 21 Drawing Sheets

FIG. 8
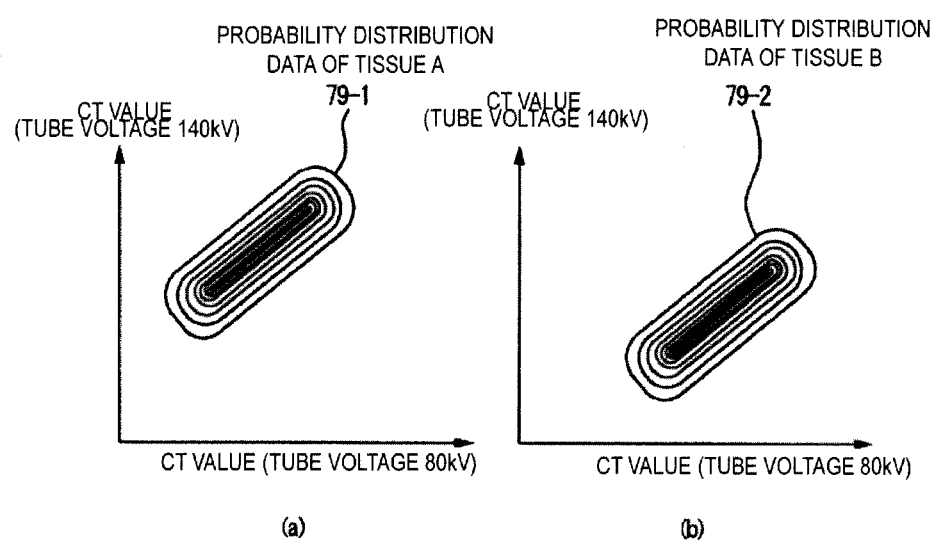
(a)  (b)
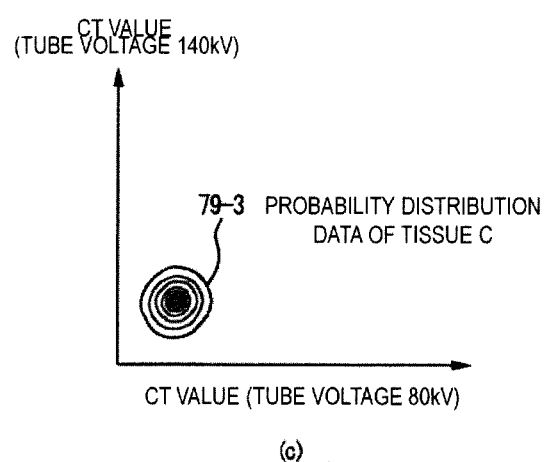
(c)

MEDICAL IMAGE PROCESSING DEVICE, METHOD FOR PROCESSING MEDICAL IMAGE AND PROGRAM

TECHNICAL FIELD

The present invention relates to a medical image processing device for processing and displaying medical image information acquired by a medical imaging apparatus such as an X-ray CT apparatus or the like. Specifically, it relates to a medical image processing device for displaying medical image information based on two or more different energy intensities.

BACKGROUND ART

A medical image picked up by an X-ray CT apparatus does not have any unique CT value irrespective of the same type of a biomedical tissue due to influence of photon noise, system noise, a beam hardening effect or the like, and thus the dispersion of the CT value takes on a normal distribution having a representative value such as an average CT value or the like at the center thereof.

The X-ray absorption factor of each biomedical tissue when an examinee is irradiated with X-ray is dependent on the energy intensity of the irradiated X-ray. Accordingly, even when different types of biomedical tissues have X-ray absorption factors having the same level under irradiation of X-ray having some energy intensity, they have different X-ray absorption factors under irradiation of X-ray having another energy intensity.

There is a method of irradiating X-ray having different energy intensities by changing an image pickup tube voltage to pick up an image in order to discriminate the type of the biomedical tissue. For example, even in a case where different types of biomedical tissues have the same level of CT values on a reconstructed image when imaging is executed by setting the tube voltage to 120 kV, the contrast difference therebetween in the reconstructed image is increased when imaging is executed with the tube voltage of 80 kV or 140 kV, and thus the types of individual biomedical tissues can be discriminated.

According to a multi-energy type X-ray CT apparatus (MECT: Multi-Energy Computed Tomography), while one or more X-ray sources and one or more X-ray detectors disposed so as to confront the X-ray source(s) are rotated, an examinee is irradiated with X-ray from the X-ray source(s) to image the examinee disposed between the X-ray source and the X-ray detector. The multi-energy type X-ray CT apparatus is a medical imaging apparatus for detecting examinee-transmitted X-ray having two or more different energy intensities by the X-ray detector(s) to obtain transmitted X-ray information and reconstructed image information.

An apparatus for measuring bone density uses a DEXA (Dual Energy X-ray Absorptionmergy) method for irradiating X-rays having two different energy intensities and taking the difference therebetween to obtain the bone density. Furthermore, an X-ray CT apparatus uses a method of discriminating bone and a contrast blood vessel, contrast blood vessel and calcification in the blood vessel or the like by using examinee-transmitted X-ray information of two or more different energy intensities which are picked up by MECT (for example, see "Patent Document 1", "Patent Document 2").

Furthermore, there is known a method (for example, see "Non-patent Document 1") for creating a map having CT values under high energy at the X-axis and CT values under low energy at the Y-axis on the basis of image information obtained by multi-energy imaging, and discriminating the type of a biomedical tissue by referring the map concerned. For example, when bone and contrast agent are discriminated from each other, a distribution area of bone and a distribution area of contrast agent on a map are sectioned from each other by a straight line. CT values of reconstructed image information obtained by multi-energy imaging are projected onto the map concerned, and a biomedical tissue located in the bone area is identified as "bone" while a biomedical tissue located in the contrast agent area is identified as "contrast agent". The identified biomedical tissues are individually colored every biomedical tissue type and displayed with being superimposed on an original image.

Furthermore, there is a method for allocating colors in accordance with the CT value ratio between image information based on high energy intensity imaging and image information based on low energy intensity imaging (CT value based on low energy intensity/CT value based on high energy intensity) and displaying the colored image information while the image information is superimposed on an original image (for example, see "Non-patent document 2").

PRIOR ART DOCUMENT

Patent Document
  Patent Document 1: JP-A-2004-174253
  Patent Document 2: JP-A-2004-065975
Non-Patent Document
  Non-patent document 1: "Dual Source CT: SOMATOM Definition, State of the Art in Cardiac-CT and Dual Energy Imaging", Video Information vol. 39, no. 7, pp 132-137
  Non-patent Document 2: "Concerning Development of High-speed Switching/Dual Energy Imaging Method—Imaging and Visualizing Method—", Japanese Society of Radiation Technology, pre-papers of the 63rd Academic general assembly meeting, pp 216

SUMMARY OF THE INVENTION

Problem to be Solved by the Invention

According to a first invention for attaining the above-described object, a medical image processing device for making a display device display medical image information based on two or more different energy intensities obtained by irradiating an examinee with X-ray is characterized by comprising: statistic amount information acquiring means for acquiring statistic amount information corresponding to a type of a biomedical tissue of the examinee every energy intensity; identification map creating means for creating an identification map for identifying the type of the biomedical tissue on the basis of the statistic amount information; tissue identifying means for identifying the type of the biomedical tissue in the acquired medical image information on the basis of the identification map; and display means for making the display device display an identification result of the tissue identifying means as the medical image information.

The medical image processing device of the first invention acquires the statistic amount information corresponding to the type of the biomedical tissue of the examinee every energy intensity to create the identification map, identifies the type of the biomedical tissue in the acquired medical image information on the basis of the identification map and makes the display device display the identified type.

The medical image information is transmitted X-ray information of the examinee picked up by a medical imaging apparatus such as an X-ray CT apparatus or the like and reconstructed image information representing a tomogram.

X-rays having different energy intensities can be generated from the X-ray source by changing the image pickup tube voltage of the X-ray CT apparatus.

The statistic amount information contains an average CT value set as transmitted X-ray information concerning a given biomedical tissue and a standard deviation of CT values. The statistic amount information is set every combination of the type of the biomedical tissue and the energy intensity to be irradiated.

The type of the biomedical tissue means a blood vessel area, a bone area, a fat area, etc.

In the first invention, the medical image processing device can identify the type of the biomedical tissue in the medical image information with high precision by the identification map created on the basis of the statistic amount information corresponding to the type of the biomedical tissue of the examinee.

The medical image processing device may create an identification probability map representing an identification degree of the biomedical tissue on the basis of the statistic amount information and the identification map, and the tissue identifying means may further acquire an identification probability value of the biomedical tissue on the basis of the identification probability map to acquire the identification degree of the biomedical tissue.

Accordingly, a display expressing the identification degree of the biomedical tissue is enabled. For example, a method of displaying an erroneously recognized area due to an effect of noise or the like, a display style, etc. can be discriminated from a method of displaying an area having a high identification degree. For example, an area having a low identification degree may be displayed to be low in brightness.

Furthermore, the type of a biomedical tissue having the highest existence probability value may be selected every area corresponding to the combination of respective statistic amount information at two or more different energy intensities to create an identification map.

It is desired to set an identifier for identifying the type of a selected biomedical tissue every area on the identification map. The identifier may be a flag, a numerical value, a symbol or the like for identifying the type.

Furthermore, the identification probability value may be set on the basis of the existence probability value of the biomedical tissue and the distance from a boundary of the type determined from the identification map to an area to create the identification probability map.

Accordingly, the identification probability value for determining the identification degree of the biomedical tissue is associated with existence probability values of plural types in consideration of the distance from the boundary of the type, and calculated with high precision.

Furthermore, the tissue identifying means may acquire medical image information, determine an identifier set every area on the basis of the identification map and identify the type of a biomedical tissue every area.

The tissue identifying means may acquire medical image information, identify the type of a biomedical tissue every area on the basis of the identification map, and further acquire an identification probability value of the biomedical tissue every area on the basis of the identification probability map.

Furthermore, the type of the biomedical tissue identified by the tissue identifying means may be displayed while a different color is set every type of the biomedical tissue.

Furthermore, the type of the biomedical tissue identified by the tissue identifying means may be displayed while a different color is set every type of the biomedical tissue, and further a gradation is set in accordance with an identification probability value of the biomedical tissue of each area obtained by the tissue identifying means.

According to a second invention, a medical image processing method for a medical image processing device for making a display device display medical image information based on two or more different energy intensities acquired by irradiating an examinee with X-ray is characterized by comprising: a statistic amount information acquiring step for acquiring statistic amount information corresponding to a type of a biomedical tissue of the examinee every energy intensity; an identification map creating step for creating an identification map for identifying the type of the biomedical tissue on the basis of the statistic amount information; a tissue identifying step for identifying the type of the biomedical tissue in the acquired medical image information on the basis of the identification map; and a display step for making the display device display an identification result of the tissue identifying step as the medical image information.

The second invention is an invention relating to the medical image processing method for the medical image processing device of the first invention.

A third invention is a program for making a computer function as a medical image processing device comprising: statistic amount information acquiring means for acquiring statistic amount information corresponding to a type of a biomedical tissue of the examinee every energy intensity; identification map creating means for creating an identification map for identifying the type of the biomedical tissue on the basis of the statistic amount information; tissue identifying means for identifying the type of the biomedical tissue in the acquired medical image information on the basis of the identification map; and display means for making the display device display an identification result of the tissue identifying means as the medical image information.

The third invention is an invention relating to the program for making a computer function as the medical image processing device of the first invention.

Effect of the Invention

According to the invention, there can be provided a medical image processing device that can identify the type of a biomedical tissue with high precision and display an identification degree with respect to medical image information in multi-energy imaging.

BRIEF DESCRIPTION OF THE DRAWINGS

[FIG. 8] is a diagram showing a probability distribution data of a tissue.

MODES FOR CARRYING OUT THE INVENTION

Figure 1:
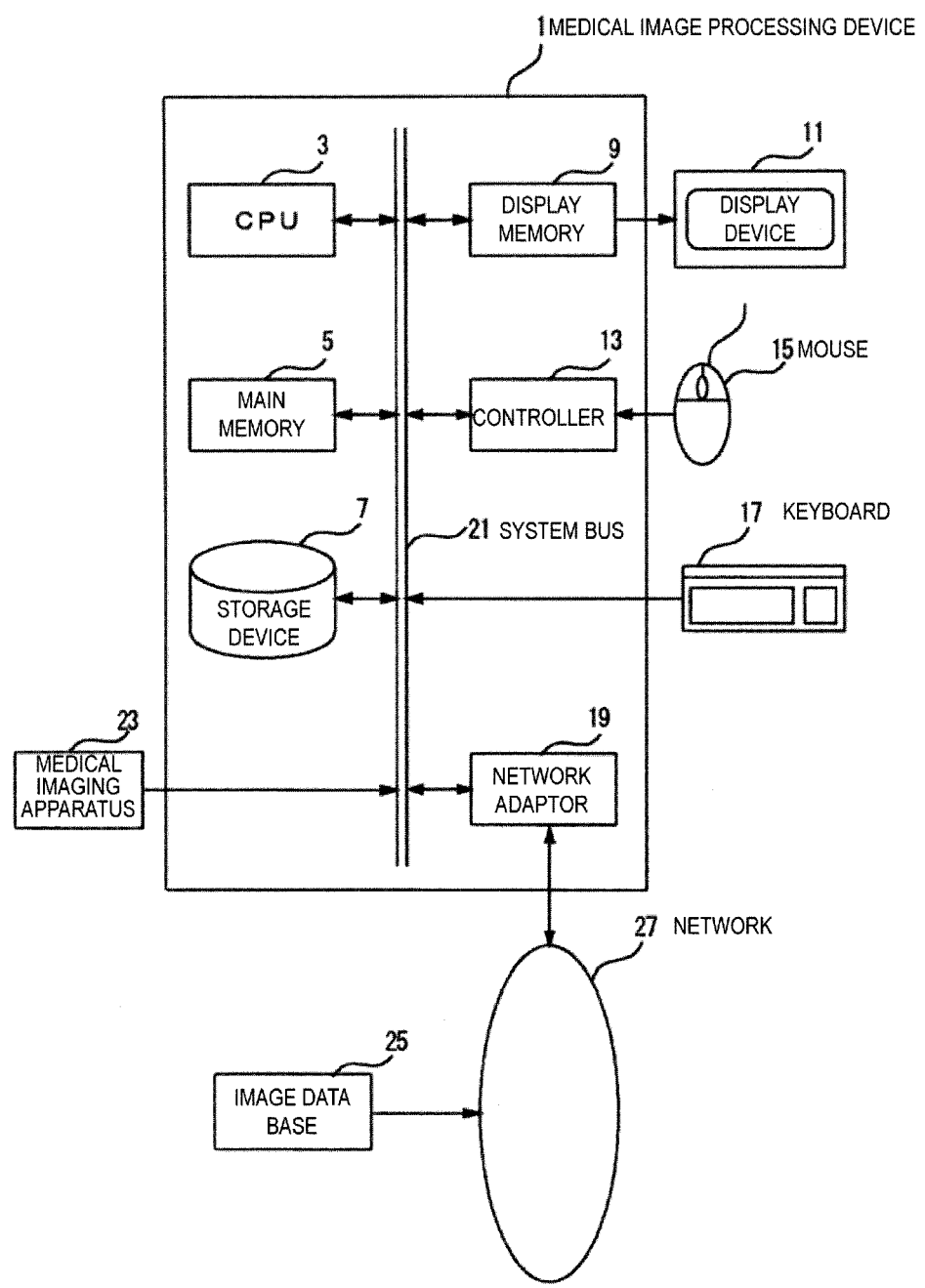
[FIG. 1] is a hardware construction diagram of a medical image processing device 1.

Preferable embodiments according to the present invention will be described in detail with reference to the accompanying drawings. In the following description and the accompanying drawings, the constituent elements having the same functional constructions are represented by the same reference numerals and the duplicative descriptions thereof are omitted. In the embodiments described below, the description will be made on the assumption that multi-energy imaging of an examinee is mainly executed by an X-ray CT apparatus and image processing of acquired medical image information is executed.

(1. Construction of Medical Image Processing Device 1)

First, the construction of the medical image processing device 1 will be described with reference to FIG. 1.

FIG. 1 is a hardware construction diagram of a medical image processing device 1.

The medical image processing device 1 is constructed by connecting, through a system bus 21, CPU 3, a main memory 5, a storage device 7, a display memory 9, a display device 11, a mouse 15 and a keyboard 17 connected to a controller 13 and a network adaptor 19. The medical image processing device 1 is connected to an image data base 25 through a network 27. Furthermore, the medical image processing device 1 is connected to a medical imaging apparatus 23 so that data can be transmitted and received therebetween. The medical imaging apparatus 23 may be connected to the medical image processing device 1 through the network 27.

CPU 3 is a device for controlling the operation of each constituent element. CPU 3 loads a program stored in the storage device 7 and data necessary for execution of the program into the main memory 5 to execute the program. The storage device 7 is a device for acquiring and storing medical image information picked up by the medical imaging apparatus 23 through the network 27 such as LAN (Local Area Network) or the like. In the storage device 7 are stored programs to be executed by CPU 3 and data required to execute the programs. The main memory 5 stores programs to be executed by CPU 3 and intermediate steps of the calculation processing.

The mouse 15 and the keyboard 17 are operating devices with which an operator instructs an operation on the medical image processing device 1. The display memory 9 stores display data to be displayed on the display device 11 such as a liquid crystal display, CRT or the like. The controller 13 detects the state of the mouse 15 to detect the position of a mouse pointer on the display device 11 and outputs a detection signal to CPU 3. The network adaptor 19 is used to connect the medical image processing device 1 to the network 27 such as LAN, a telephone line, the Internet or the like.

The medical imaging apparatus 23 is an apparatus for picking up medical image information such as a tomogram or the like of an examinee. The medical imaging apparatus 23 is an X-ray CT apparatus, an X-ray fluoroscopic apparatus, an MRI apparatus or an ultrasonic imaging apparatus, for example.

The image database 25 is a data base system for storing medical image information picked up by the medical imaging apparatus 23. The image data base 25 may accumulate medical image information picked up by plural other medical imaging apparatuses connected to the network 27.

(2. Construction of Medical Imaging Apparatus 23)

Next, the construction of the medical imaging apparatus 23 will be described with reference to FIG. 2.

Figure 2:
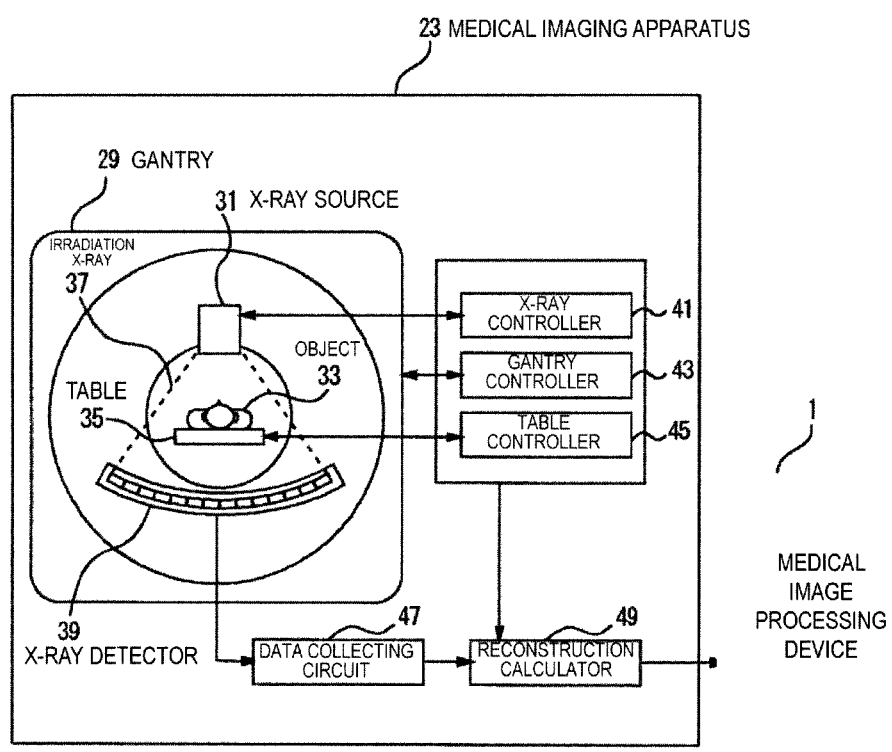
[FIG. 2] is a hardware construction diagram showing a medical imaging apparatus 23.

FIG. 2 is a hardware construction diagram showing the medical imaging apparatus 23.

The construction of a multi-energy type X-ray CT apparatus as the medical imaging apparatus 23 will be described. The medical imaging apparatus 23 comprises a gantry 29, an X-ray source 31 and an X-ray detector 39 mounted in the gantry 29, a table 35 on which an examinee 33 is put, an X-ray controller 41 for controlling irradiation X-ray 37, a gantry controller 43 for controlling the gantry 29, a table controller 45 for controlling the table 35, a data collecting circuit 47 for collecting transmitted X-ray information detected by the X-ray detector 39, a reconstruction calculator 49 for executing reconstructing calculation of collected data, etc. The reconstructed image information reconstructed by the reconstruction calculator 49 is supplied to the medical image processing device 1. The reconstructed image information may be accumulated in the image data base 25 through the storage device 7 of the medical image processing device 1 or the network 27.

The X-ray source 31 applies X-ray to the X-ray detector 39 which is disposed so as to confront the X-ray source 31 through the examinee 33. The X-ray detector 39 detects X-ray transmitted through the examinee 33. The X-ray source 31 and the X-ray detector 39 rotate around the examinee 33 during one scanning.

The multi-energy type X-ray CT apparatus acquires transmitted X-ray information when the same examinee is irradiated with X-rays having two or more different energy intensities. The multi-energy type X-ray CT apparatus has two or more X-ray sources 31 and X-ray detector (s) 39 in the gantry 29, and applies different tube voltages to the respective X-ray sources 31 to perform multi-energy imaging. The details of the multi-energy imaging will be described later.

The X-ray controller 41 controls the X-ray sources 31. The X-ray controller 41 supplies the X-ray sources 31 with a power signal for controlling the tube voltage, an X-ray generating timing signal, etc.

The gantry controller 43 controls the rotational speed, the position, etc. of the X-ray sources 31 and the X-ray detectors 39 disposed in the gantry 29.

The table controller 45 controls the moving speed and position of the table 35 on which the examinee 33 is put.

The data collecting circuit 47 collects transmitted X-ray information detected by the X-ray detector 39, converts the analog signal thereof to a digital signal and supplies the digital signal to the reconstruction calculator 49.

The reconstruction calculator 49 executes image reconstruction processing on the transmitted X-ray information transmitted from the data collecting circuit 47 to create a tomographic image (reconstructed image) of the examinee. The reconstruction calculator 49 sends the reconstructed image to the medical image processing device 1.

(3. Operation of Medical Image Processing Device 1)

Next, referring FIG. 3, a description will be given of the operation of the medical image processing device 1 for identifying the types of plural biomedical tissues on the basis of multi-energy imaging information and visualizing and displaying the identification degree every tissue.

Figure 3:
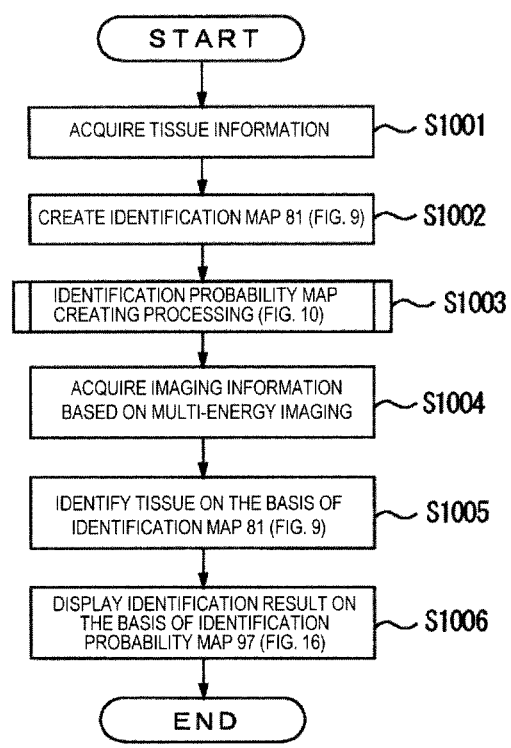
[FIG. 3] is a flowchart showing the overall operation of the medical image processing device 1.

FIG. 3 is a flowchart showing the overall operation of the medical image processing device 1. The multi-energy imaging information will be described hereunder as imaging information when the tube voltage is equal to 140 kV under high energy and as imaging information when the tube voltage is equal to 80 kV under low energy. The value of the tube voltage is not limited to these values.

(3-1. Acquisition of Tissue Information)

CPU 3 of the medical image processing device 1 reads through an operator's input based on a pointing device such as the mouse 15, the keyboard 17 or the like or an external input device to acquire statistical amount information corresponding to a biomedical tissue to be identified, that is, values such as an average CT value, a standard deviation representing the variation of CT values, etc. (step 1001).

Figure 4:
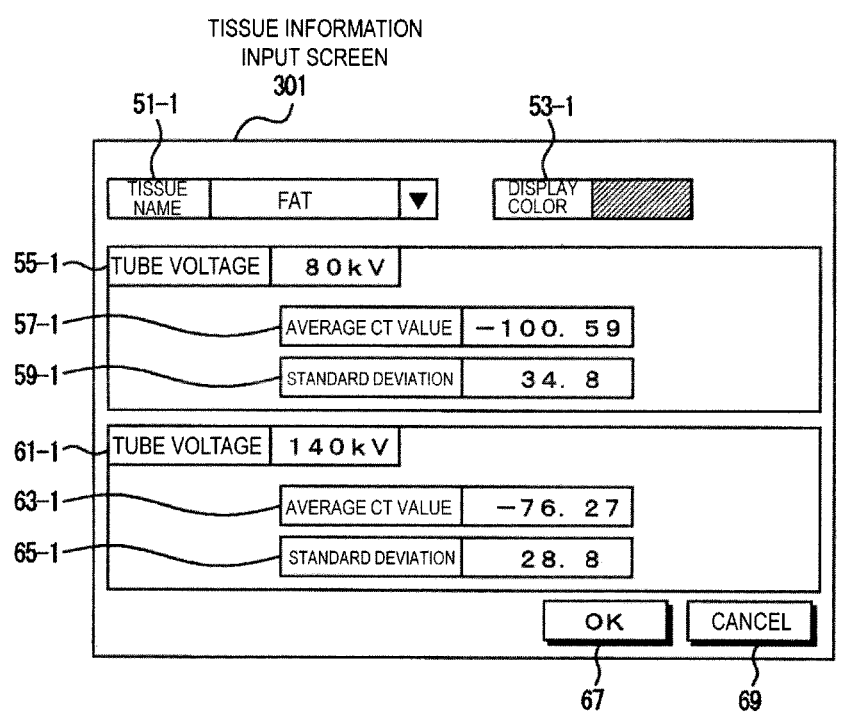
[FIG. 4] is a diagram showing a tissue information input screen 301.

FIG. 4 is a diagram showing a tissue information input screen 301 for inputting information concerning a biomedical tissue by the operator. The tissue information input screen 301 is displayed on the display device 11. Input frames for a tissue name 51-1 of a biomedical tissue, a display color 53-1, a tube voltage 55-1 under low energy and a tube voltage 61-1 under high energy are arranged on the tissue information input screen 301. Furthermore, input frames for the statistic amount information of the biomedical tissue input through the tissue name 51-1, that is, the average CT value 57-1 and the average CT value 63-1 of each tube voltage, and the standard deviation 59-1 and the standard deviation 65-1 of CT values are arranged.

As the display color 53-1 is set at least any one of a color and a pattern which represent an area corresponding to the tissue name 51-1 of the medical image information picked up by the multi-energy type X-ray CT apparatus.

The operator inputs the tissue name 51-1, the display color 53-1 when display is executed every biomedical tissue, statistic amount information of the biomedical tissue, etc. on the tissue information input screen 301.

When "OK" button 67 is pushed, an input content is determined. When "cancel" button 69 is pushed, the input content is canceled. CPU 3 stores the determined input content into the storage device 7 or the like.

Figure 5:
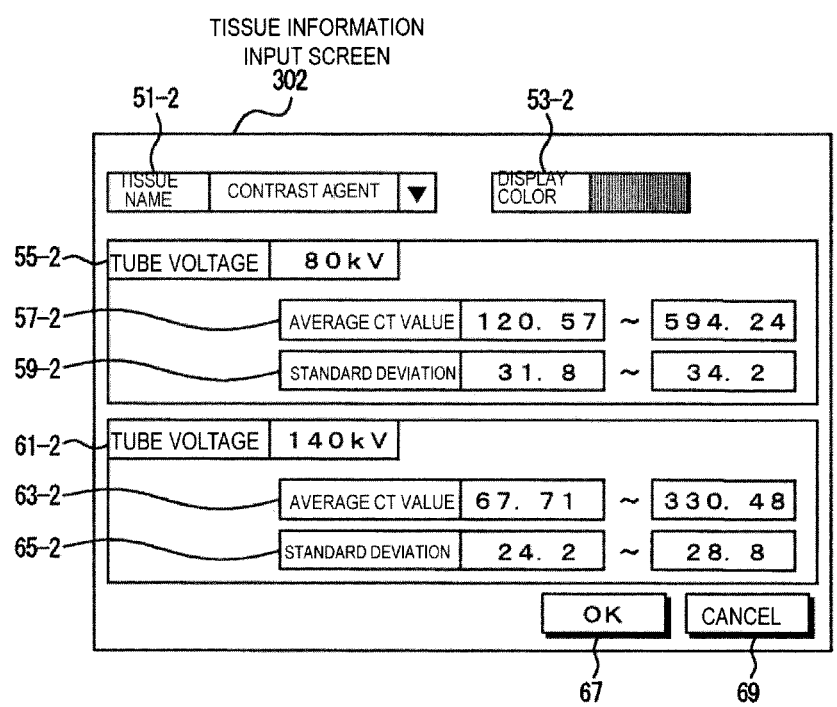
[FIG. 5] is a diagram showing a tissue information input screen 302.

FIG. 5 is a diagram showing the tissue information input screen 302 when tissue information containing an average CT value having a width due to concentration like contrast agent or the like is input. On the tissue information input screen 302 are arranged input frames for a tissue name 51-2 of a biomedical tissue, a display color 53-2, a tube voltage 55-2 under low energy and a tube voltage 61-2 under high energy. The respective upper limit values and lower limit values of an average CT vale 57-2 at the tube voltage 55-2 under low energy, a standard deviation 59-2 of CT values, an average CT value 63-2 at the tube voltage 61-2 under high energy, and a standard deviation 65-2 are arranged.

The tissue information input screen shown in FIGS. 4 and 5 are examples of the screen construction for inputting the information corresponding to a biomedical tissue, however, the present invention is not limited to this screen construction. The tissue information input screen may be a screen for inputting information such as the name of a biomedical tissue to be identified, an average CT value, a standard deviation of CT values, etc.

As described above, the medical image processing device 1 acquires the display color and the statistic amount information such as the average CT value, the standard deviation of CT values, etc. under application of X-ray having a predetermined energy intensity every biomedical tissue. The setting of the display color and the statistic amount information for each biomedical tissue may be acquired from information pre-registered in the medical image processing device 1 or acquired through the network 27.

(3-2. Creation of Identification Map 81)

Subsequently, the medical image processing device 1 creates an identification map on the basis of tissue information of each biomedical tissue acquired in step 1001 (step 1002). The identification map is used when the type of the biomedical tissue is identified from medical image information (transmitted X-ray information or reconstructed image information) acquired from the medical imaging apparatus 23.

The creation of the identification map will be described with reference to FIGS. 6 to 9.

Figure 6:
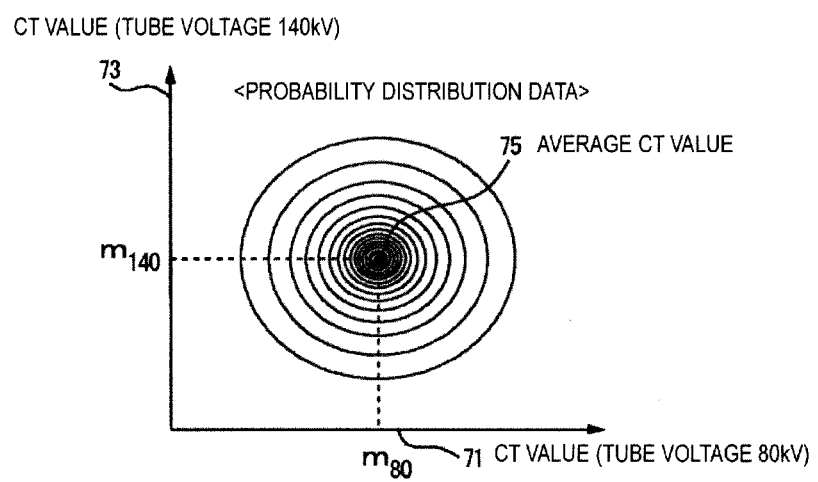
[FIG. 6] is a diagram showing the correspondence between probability distribution data and statistical amount information.

FIG. 6 is a diagram showing the correspondence between probability distribution data and statistic amount information. The probability distribution data are calculated on the basis of the statistic amount information of the predetermined biomedical tissue which is acquired in step 1001. In FIG. 6, CT values under the tube voltage of 80 kV are set on the X-axis, and CT values under the tube voltage of 140 kV are set on the Y-axis. The probability distribution data are calculated by approximation using a two-dimensional Gaussian distribution as shown in mathematical expression (1).

[Mathematical Expression 1]

$$g(i, j) = \frac{1}{\sqrt{2\pi} \cdot \sigma_{80} \cdot \sigma_{140}} \exp\left\{-\frac{(i - m_{80})^2}{2\sigma_{80}^2} - \frac{(j - m_{140})^2}{2\sigma_{140}^2}\right\} \quad (1)$$

Here, i, j: x-coordinate, y-coordinate on probability distribution data $\sigma_{80}$: standard deviation of CT values under tube voltage of 80 kV $\sigma_{140}$: standard deviation of CT values under tube voltage of 140 kV $m_{80}$: average CT value under tube voltage of 80 kV $m_{140}$: average CT value under tube voltage of 140 kV The values calculated by the mathematical expression (1) are imaged to obtain the probability distribution data shown in FIG. 6. The value g(i,j) of the coordinate at the average CT value ($m_{80}$) under tube voltage of 80 kV and the average CT value ($m_{140}$) under tube voltage of 140 kV is highest, and the value g(i,j) of the coordinate decreases gently as the coordinate shifts to the periphery. The value g(i,j) of the coordinate corresponds to an existence probability value. In FIG. 6, a distribution condition is expressed by connecting portions having an equal existence probability value.

FIG. 6 shows the probability distribution data when one average CT value is settled as shown on the tissue information input screen 301 (FIG. 4).

Next, a method of creating probability distribution data when the CT value has a width due to a condition such as concentration or the like as in the case of contrast agent or the like which is input through the tissue information input screen 302 (FIG. 5) will be described.

Figure 7:
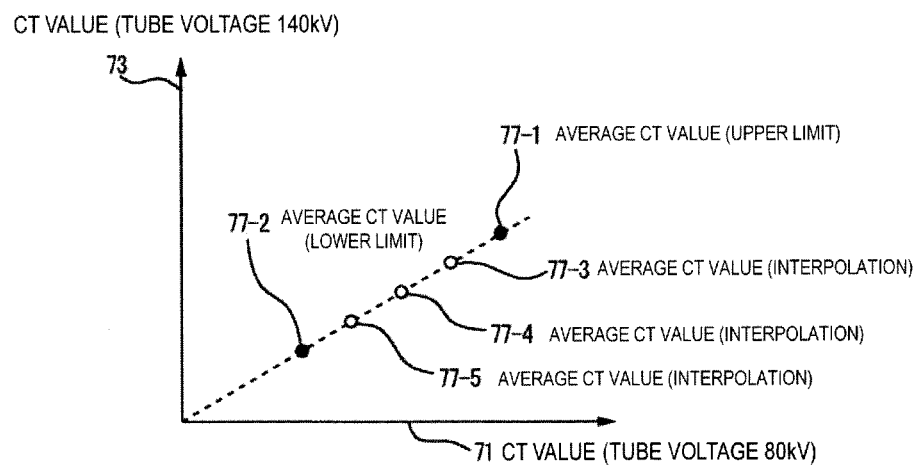
[FIG. 7] is a diagram showing a probability distribution data creating method when a CT value has a width.

FIG. 7 shows a method of creating probability distribution data when the CT value has a width. In FIG. 7, the upper limit value and the lower limit value of the average CT value input through the tissue information input screen 302 (FIG. 5) are plotted on the drawing, and they are set as an average CT value (upper limit) 77-1 and an average CT value (lower limit) 77-2. The average CT value (upper limit) 77-1 and the average CT value (lower limit) 77-2 are connected to each other with a straight line, and a predetermined number of interpolation points on this line are set as an average CT value (interpolation) 77-3, an average CT value (interpolation) 77-4 and an average CT value (interpolation) 77-5.

The probability distribution is calculated for each of the average CT value (upper limit) 77-1, the average CT value (lower limit) 77-2, the average CT value (interpolation) 77-3, the average CT value (interpolation) 77-4 and the average CT value (interpolation) 77-5 according to the above mathematical expression (1), data representing the maximum probability value is selected with respect to each coordinate, and the probability distribution data are created. The acquired probability distribution data have a rod-like shape as shown in FIG. 8(a), for example.

FIG. 8 is a diagram showing the probability distribution data of a tissue. FIG. 8(a) shows probability distribution data 79-1 of a tissue A, FIG. 8(b) shows probability distribution data 79-2 of a tissue B and FIG. 8(c) shows probability distribution data 79-3 of a tissue C. The tissue A, the tissue B and the tissue C represent different types of biomedical tissues. Furthermore, the tissue A and the tissue B whose probability distribution data represent rod-like shapes are tissues when CT values thereof have widths in accordance with conditions. In FIG. 8, a distribution condition is illustrated by connecting portions having equal existence probability values with lines.

Subsequently, the medical image processing device 1 compares the probability distribution data of the respective tissues with respect to all the common coordinates of the probability distribution data 79-1 of the tissue A, the probability distribution data 79-2 of the tissue B and the probability distribution data 79-3 of the tissue C, and sets the identifier (flag) corresponding to the tissue having the highest probability (existence probability value) at each coordinate. The identifiers (flags) are set for all the coordinates, and set as an identification map 81. The identifier may be a flag, a numerical value, a character array or the like for identifying the type of the tissue.

Figure 9:
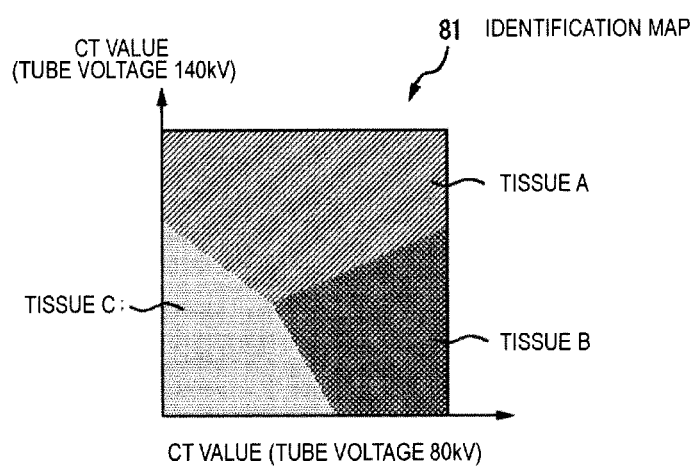
[FIG. 9] is a diagram showing an identification map 81.

FIG. 9 is a diagram showing the identification map 81. With respect to a tissue taking on the combination of predetermined CT value (tube voltage 80 kV) and CT value (tube voltage 140 kV), the type of the corresponding tissue (the tissue A, the tissue B or the tissue C) can be identified by referring to the identification map 81.

(3-3. Processing of Creating Identification Probability Map)

Subsequently, the medical image processing device 1 creates the identification probability map on the basis of the statistic amount information (average CT value and the standard deviation of the CT values) of the biomedical tissue acquired in step 1001 and the identification map 81 created in step 1002 (step 1003). The identification probability map is a map to be referred to in order to acquire the identification degree with respect to a tissue taking on the combination of predetermined CT value (tube voltage 80 kV) and CT value (tube voltage 140 kV). The details of the identification probability map creating processing will be described with reference to FIGS. 10 to 16.

Figure 10:
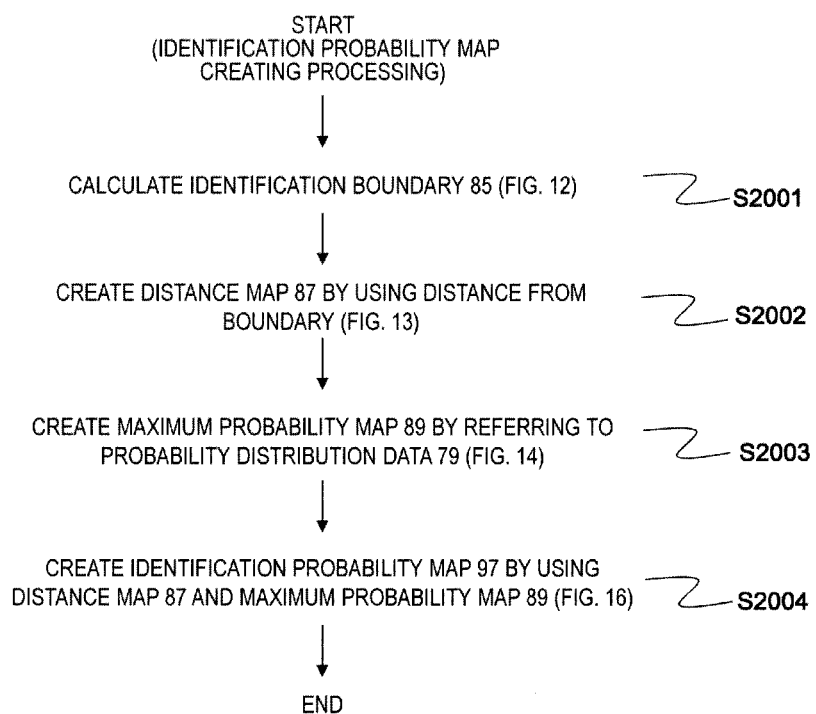
[FIG. 10] is a flowchart showing the processing of creating an identification probability map 97.
Figure 16:
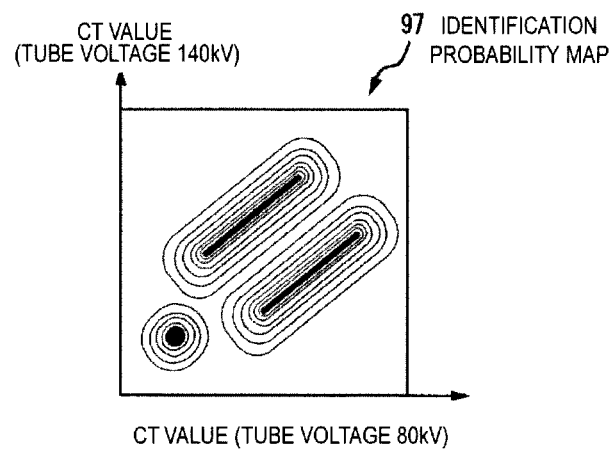
[FIG. 16] is a diagram showing an identification probability map 97.

FIG. 10 is a flowchart showing the processing of creating the identification probability map 97 shown in FIG. 16.

The processing of creating the identification probability map 97 will be described hereunder with reference to FIG. 10.

(3-3-1. Identification Boundary Calculation Processing)

The medical image processing device 1 calculates an identification boundary 85 of each tissue area on the basis of the identification map 81 created in step 1002 (step 2001).

Figure 11:
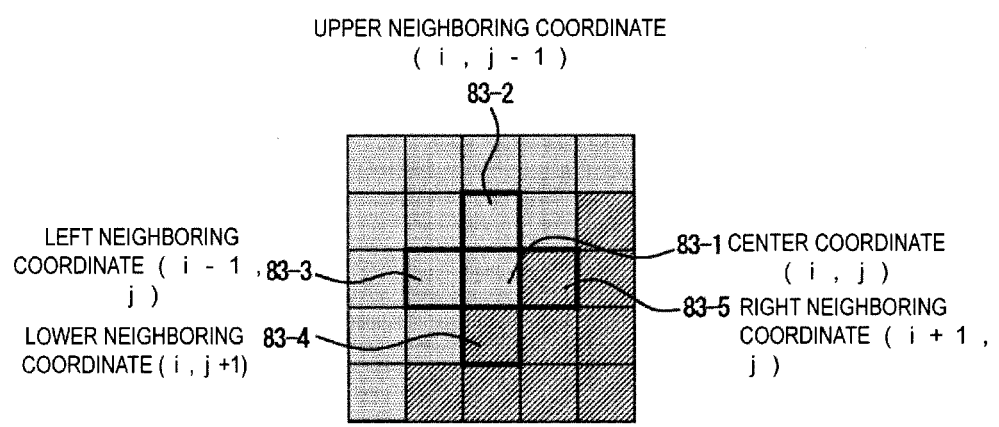
[FIG. 11] is a diagram showing boundary calculation processing.

FIG. 11 is a diagram showing the boundary calculation processing. FIG. 11 is an enlarged view of coordinates of some area on the identification map 81 (FIG. 9). A prescribed coordinate is noted, and a center coordinate (i,j) 83-1 is set. The identifiers (flags) of tissues at four neighboring coordinates (upper neighboring coordinate (i,j−1) 83-2, left neighboring coordinate (i−1, j) 83-3, lower neighboring coordinate (i,j+1) 83-4 and right neighboring coordinate (i+1, j) 83-5) at the upper, lower, right and left sides of the center coordinate (i,j) 83-1 are referred to.

If at least one of the identifiers of the tissues at the four neighboring coordinates is different from the identifier of the center coordinate (i,j) 83-1, the center coordinate is recognized as a boundary. The above boundary calculation processing is executed on all the coordinates of the identification map 81 to acquire the identification boundary 85.

Figure 12:
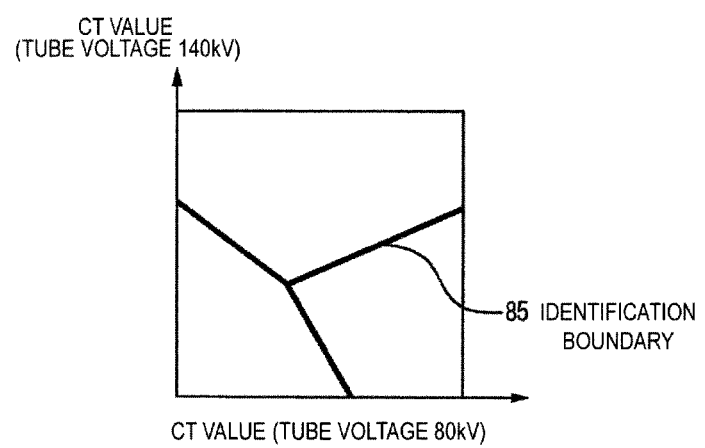
[FIG. 12] is a diagram showing an identification boundary 85.

FIG. 12 is a diagram showing the identification boundary 85. For example, a flag representing a boundary is set at the coordinate corresponding to the identification boundary 85 of FIG. 12, for example.

(3-3-2. Creation of Distance Map)

Subsequently, the medical image processing device 1 calculates the distance from the identification boundary 85 in the same coordinate system as the probability distribution data (for example, FIG. 6, FIG. 8) on the basis of the identification boundary 85 acquired in step 2001 to create a distance map 87 (step 2002). The distance from the identification boundary 85 to the coordinate is determined by using Euclidean distance conversion, for example. The distance from the identification boundary 85 is set for all the coordinates, and the distance map 87 is created.

Figure 13:
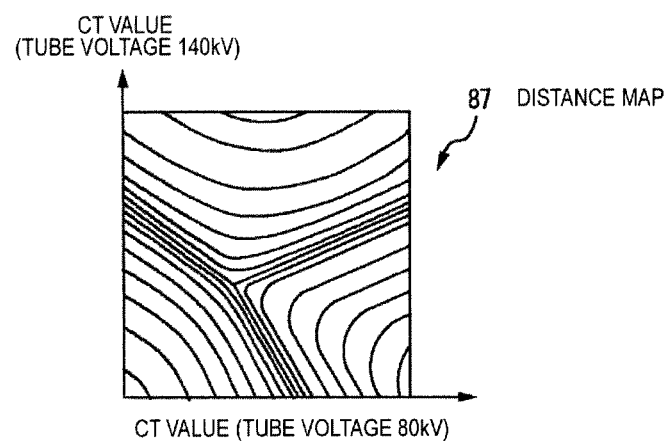
[FIG. 13] is a diagram showing a distance map 87.

FIG. 13 is a diagram showing the distance map 87.

A distance "0" is set at the coordinates on the identification boundary 85. In FIG. 13, portions which are located at the same distance from the identification boundary 85 are connected to one another by a line.

(3-3-3. Creation of Maximum Probability Map 89)

Subsequently, the medial image processing device 1 refers to the probability distribution data 79 (FIG. 8) to create a maximum probability map 89 (step 2003). That is, the medical image processing device 1 compares the probability distribution data of the respective biomedical tissues (the probability distribution data 79-1 of the tissue A, the probability distribution data 79-2 of the tissue B, the probability distribution data 79-3 of the tissue C) so that the existence probability value of the tissue representing the highest existence probability value at the same coordinate is selected as the maximum probability value of the coordinate concerned. Irrespective of the type of the biomedical tissue, the maximum probability value is set with respect to each coordinate, and the maximum probability map 89 is created.

Figure 14:
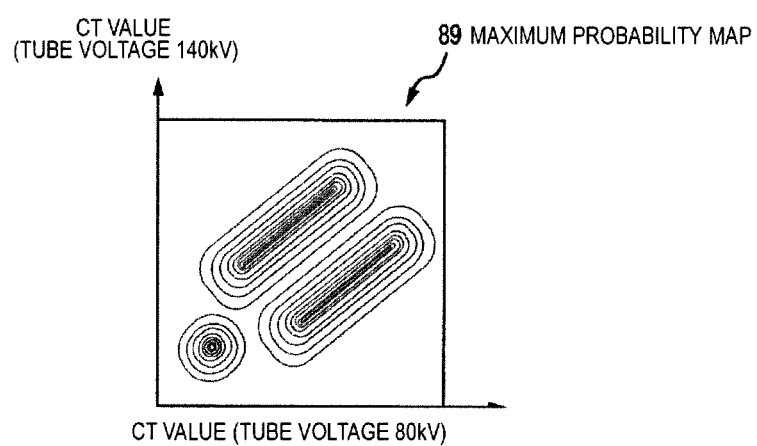
[FIG. 14] is a diagram showing a maximum probability map

FIG. 14 is a diagram showing the maximum probability map 89. In the maximum probability map 89, an existence probability value is set with respect to each coordinate, and it is impossible to identify the type of the biomedical tissue. In FIG. 14, in order to enhance visibility, portions having equal existence probability values are connected by a straight line every type of the biomedical tissue.

(3-3-4. Creation of Identification Probability Map 97)

Subsequently, the medical image processing device 1 crates the identification probability map 97 by using the distance map 87 created in step 2002 and the maximum probability map 89 created in step 2003 (step 2004). A value representing the identification degree of each coordinate is set at each coordinate of the identification probability map 97. It is assumed that values from "0" to "255" are set as identification probability values r at the respective coordinates of the identification probability map 97 as in the case of the gradation of the color.

The values at the same coordinate are acquired from the distance map 87 and the maximum probability map 89. A distance value d(i,j) is acquired from the distance map 87, an existence probability value p(i,j) is acquired from the maximum probability map 89. The distance value d(i,j) is the distance from the boundary, and the existence probability value p(i,j) is a probability value when the center value (maximum probability) of the biomedical tissue is set to "1.0". A method of calculating the identification probability value of a coordinate of interest on the basis of the distance value d(i,j) and the existence probability value p(i,j) will be described.

Figure 15:
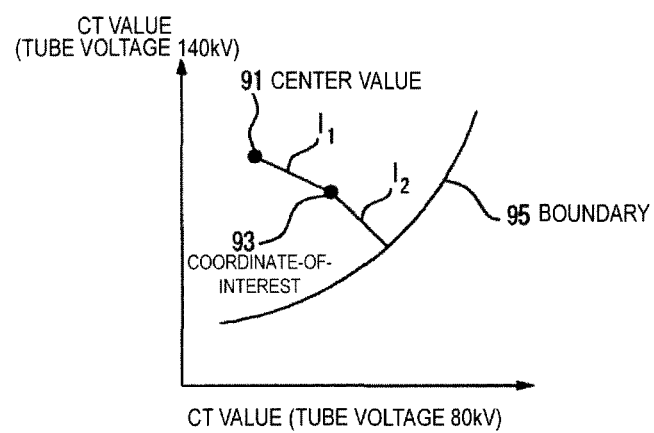
[FIG. 15] is a diagram showing the position of a coordinate-of-interest 93.

FIG. 15 is a diagram showing the position of the coordinate-of-interest 93. The distance between the center value 91 and the coordinate-of-interest 93 is represented by $l_1$, and the distance between the boundary 95 and the coordinate-of-interest 93 is represented by $l_2$. The center value 91 is determined from the maximum probability map 89, and the boundary 95 is determined from the distance map 87.

Here, $$l_1 = 1/p(i,j) - 1 \quad (2)$$

$$l_2 = d(i,j) \quad (3)$$

The identification probability value r(i,j) of the coordinate-of-interest 93 is calculated according to the following mathematical expression (4).

$$r(i, j) = 255 \times l_2 / (l_1 + l_2) \quad (4)$$
$$= 255 \times d(i, j) / [\{(1/p(i, j)) - 1\} + d(i, j)]$$

The identification probability value r is calculated and set for all the coordinates, and the identification probability map 97 is obtained.

FIG. 16 is a diagram showing the identification probability map 97. With respect to the identification probability value r in the identification probability map 97, the center value represents the maximum value "255", and the value decreases as it approaches to the boundary representing the identification probability value "0". With respect to the identification probability map 97, the identification probability values (values from 0 to 255) are set for the respective coordinates, and thus the type of the biomedical tissue cannot be identified. In FIG. 16, in order to enhance the visibility, portions having an equal identification probability value are connected to one another by a line every type of the biomedical tissue.

The method of creating the identification probability map 97 is not limited to the above-described method. For example, it may be calculated on the basis of the probability distribution based on the maximum probability map 89.

Furthermore, the distance $l_1$ from the center value 91 of the coordinate-of-interest 93 may be calculated according to the following mathematical expression (5).

$$l_1 = \ln(1/p(i,j)) \quad (5)$$

As described above, the medical image processing device 1 acquires the display color setting and the statistic amount information every biomedical tissue in advance before multi-energy imaging information is acquired, and the identification probability map 97 for attaining the identification map 81 and the identification degree to be referred to when the type of the biomedical tissue is identified (step 1001 to step 1003).

(3-4. Acquisition of Multi-Energy Imaging Information)

Subsequently, CPU 3 of the medical image processing device 1 acquires the multi-energy imaging information picked up by the medical imaging apparatus 23 from the storage device 7 or the image data base 25, and reads it into the main memory (step 1004). The multi-energy imaging information is transmitted X-ray information or reconstructed image information.

The description will be made on the assumption that the medical imaging apparatus 23 acquires imaging information at the tube voltage of 140 kV as multi-energy imaging information under high energy and also imaging information at the tube voltage of 80 kV as multi-energy imaging information under low energy.

There are various methods for multi-energy imaging of the medical imaging apparatus 23. For example, there is a method in which two or more X-ray sources 31 and an X-ray detector 39 are provided in the gantry 29, and different tube voltages are applied to the respective X-ray sources 31 to irradiate an examinee with X-rays having different energy intensities, thereby acquiring transmitted X-ray information having two or more different energy intensities. Furthermore, there is a method of arranging X-ray detectors 39 different in thickness or material in a multilayer style, whereby transmitted X-ray information having different energy intensities is acquired even when the examinee is irradiated with X-ray having a single energy intensity. Furthermore, there is a method of switching the image pickup tube voltage of the X-ray source 31 at high speed during scanning to irradiate X-ray having a different energy intensity every time the gantry 29 makes one circuit.

In this embodiment, the method of the multi-energy imaging is not limited insofar as the examinee-transmitted X-ray information having two or more different energy intensities can be obtained.

(3-5. Identification of Biomedical Tissue)

Subsequently, the medical image processing device 1 identifies the type of the biomedical tissue contained in the multi-energy imaging information on the basis of the multi-energy imaging information obtained in step 1004 and the identification map 81 created in step 1002 (step 1005).

That is, each CT value of a pixel-of-interest is acquired from each of the image information of the tube voltage 80 kV and the image information of the tube voltage 140 kV which are obtained as the multi-energy imaging information. For example, with respect to the pixel-of-interest, $CT_{80}$ is acquired as the CT value of the image information of the tube voltage 80 kV, and $CT_{140}$ is acquired as the CT value of the image information of the tube voltage 140 kV.

Figure 17:
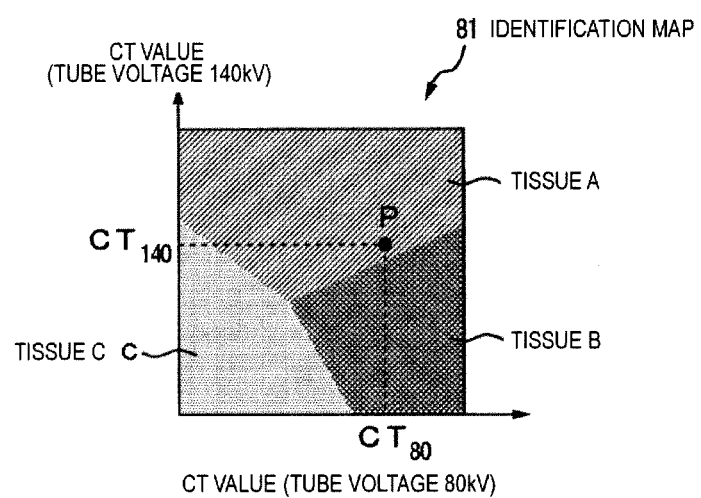
[FIG. 17] is a diagram showing projection of CT values onto the identification map 81.

FIG. 17 is a diagram showing the projection of the CT value of the pixel-of-interest onto the identification map 81. The pixel-of-interest is projected onto the identification map 81 on the basis of the CT values ($CT_{80}$, $CT_{140}$), and an identifier (flag) set at the coordinate P of the projection position is obtained. The type of the biomedical tissue can be identified on the basis of the identifier. For example, the coordinate P is identified as "tissue A" by referring to the identifier.

The medical image processing device 1 executes the identification processing with respect to all the pixels of the image information of the tube voltage 80 kV and the image information of the tube voltage 140 kV which are acquired as the multi-energy imaging information.

(3-6. Display of Identification Result)

The medical image processing device 1 displays the result identified in step 1005 on the display device 11. The identification result of the pixels of the image information is displayed while the display color 53 set every biomedical tissue when the tissue information is input (step 1001) and the identifier representing the type of the biomedical tissue acquired in the identification processing (step 1005) of the type of the biomedical tissue are associated with each other.

For example, when three tissues of bone, contrast blood vessel and soft tissue are displayed with being identified with respect to the acquired multi-energy imaging information, "red", "green" and "blue" are allocated as the display colors of the respective tissues. In this case, "red", "green" and "blue" are displayed with being superimposed on the original image when the identification result is the bone, the contrast blood vessel and the soft tissue, respectively. The image on which the display color is superimposed may be any one of an image of the tube voltage 80 kV and an image of the tube voltage 140 kV, or an image created by processing both the images.

Figure 18:
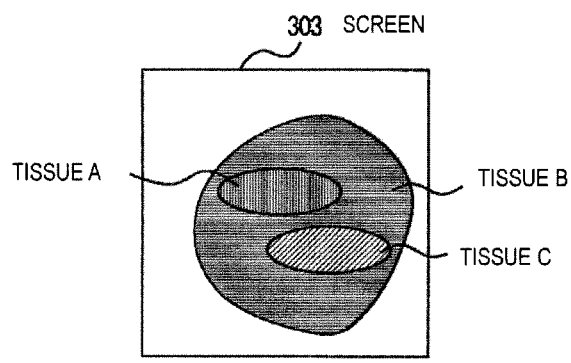
[FIG. 18] is a diagram showing a display screen 303 of a biomedical tissue.

FIG. 18 is a diagram showing a display screen 303 of the biomedical tissue.

FIG. 18 shows a tomogram of the examinee 33, and also shows the display screen 303 on which the biomedical tissues are identified as the types of the tissue A, the tissue B and the tissue C on the basis of the identification map 81 and displayed with different display colors. The biomedical tissue shown in FIG. 18 is different from the biomedical tissue described with reference to FIG. 17 and the preceding figures to FIG. 17. In FIG. 18, the difference in display color is represented by the difference in pattern.

(3-7. Effect of Display Based on Type Identification)

As described above, the medical image processing device 1 of this invention identifies the tomographic image of the examinee 33 acquired as the multi-energy imaging information every biomedical tissue type, and displays the tomographic image while colors which are different every type are superimposed on the tomographic image, so that a display screen having high visibility can be obtained. According to this embodiment, the visibility of the display image is enhanced, and thus there is an effect that the speed and precision of the medical diagnosis by medical service workers can be enhanced and medical error can be reduced.

Even when the imaging condition or the setting condition of the medical imaging apparatus 23 or the like is changed and thus the CT values or the distribution of the CT values of the biomedical tissue to be imaged varies, the medical image processing device 1 of this invention can maintain the identification performance of the biomedical tissue by changing the tissue information, so that degradation of the identification precision can be prevented.

(3-8. Identification Result Display to which Identification Degree is Reflected)

On the basis of the identification probability map 97 (FIG. 16), the medical image processing device 1 may further display the identification result to which the identification degree is reflected (step 1006).

The medical image processing device 1 acquires the respective CT values for a pixel-of-interest from the image information at the tube voltage 80 kV and the image information at the tube voltage 140 kV.

With respect to the pixel-of-interest, $CT_{80}$ is obtained as the CT value of the image information at the tube voltage 80 kV while $CT_{140}$ is obtained as the CT value of the image information at the tube voltage 140 kV, and the CT values are projected onto the identification probability map 97, thereby obtaining a identification probability value (a value from 0 to 255) set at the coordinate of the projection destination on the identification probability map 97.

The medical image processing device 1 acquires the identification probability values (the values from 0 to 255) of the biomedical tissue for all the pixels of the image information at the tube voltage 80 kV and the image information at the tube voltage 140 kV which are acquired as the multi-energy imaging information.

On the basis of the acquired identification probability values (the values from 0 to 255), the medical image processing device 1 changes brightness and color saturation with respect to the display color 53 of each biomedical tissue which is obtained in step 1001, whereby the identification degree of the biomedical tissue is expressed while reflected to the display method.

The following method is used as a method of expressing the identification degree while reflecting the identification degree to the display method.

(a) Variation of Brightness Corresponding to Identification Probability Value

There is a method of changing the brightness of the display color in accordance with the acquired identification probability value (the value from 0 to 255). For example, in a case where the display color is set to "red", according to a method of reducing the brightness as the identification probability value is smaller, the display color is "red" when the identification probability value is equal to the maximum value "255". The brightness of the display color decreases as the identification probability value is lower and thus the display color approaches to black color, so that the display color is set to "black" when the identification probability value is equal to the minimum value "0".

According to a method of increasing the brightness as the identification probability value is smaller, the display color is "red" when the identification probability value is equal to the maximum value "255". The brightness of the display color increases as the identification probability value is lower, and thus the display color approaches to white, so that the display color is set to "white" when the identification probability value is equal to the minimum value "0".

(b) Variation of Color Saturation Corresponding to Identification Probability Value There is a method of varying the color saturation of the display color in accordance with the acquired identification probability value (the value from 0 to 255). For example, in a case where the display color is set to "red", the display color is "red" when the identification probability value is equal to the maximum value "255". The color saturation of the display color decreases as the identification probability value is lower, and thus the display color approaches to gray, so that the display color is "gray" when the identification probability value is equal to the minimum value "0".

(c) Variation of Transparency Corresponding to Identification Probability Value

There is a method of changing the transparency of the display color in accordance with the acquired identification probability value (the value from 0 to 255). For example, in a case where the display color is set to "red", the display color is "red" when the identification probability value is equal to the maximum value "255". As the identification probability value is lower, the transparency increases, and the display color is perfectly transparent when the identification probability value is equal to the minimum value "0".

The foregoing (a) to (c) are the examples of the method of expressing the identification degree while the identification degree is reflected to the display method, however, the present invention is not limited to this method. Furthermore, the above display methods may be combined to express the identification degree. Still furthermore, the present invention is not limited to the display based on the combination of the identification degree and the display color as described above, and only the identification degree may be expressed (brightness, color saturation, transparency or the like may be expressed) by using the same display color for all the biomedical tissues.

(3-9. Effect of Displaying Identification Degree)

As described above, the medical image processing device 1 displays an area having a low identification probability such as noise or the like and an area having a high identification probability for which a tissue is normally recognized while stepwise discriminating these areas from each other in accordance with the identification degree. Therefore, an operator is enabled to make an accurate and rapid diagnosis for a biomedical tissue.

(3-10. Display Setting of Screen)

Figure 19:
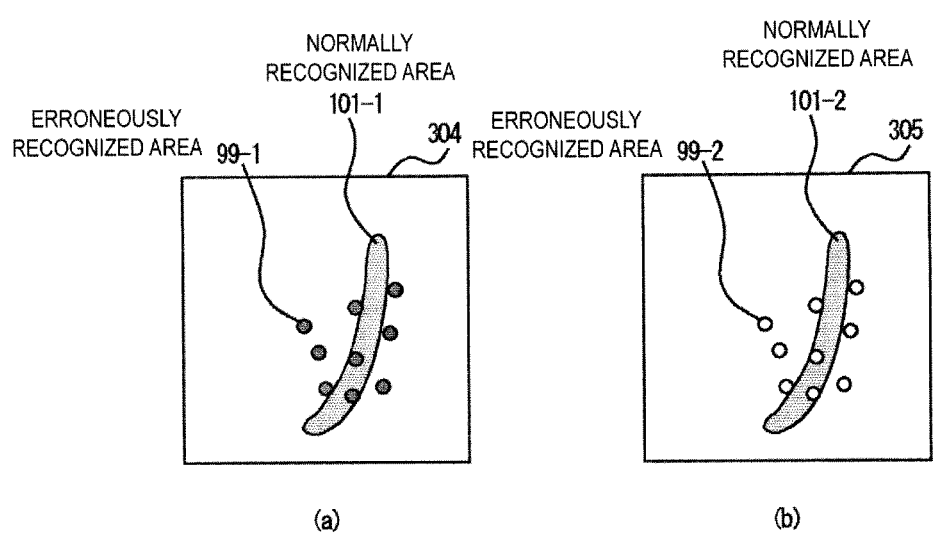
[FIG. 19] is a diagram showing display of a recognition result.

Next, a screen displayed on the display device 11 will be described with reference to FIGS. 19 to 21.

FIG. 19(a) shows a screen 304 when it is displayed irrespective of the identification degree of the biomedical tissue. An area having a low identification probability value (erroneously recognized area 99-1) is displayed on the screen with the same expression as a normally recognized area (normally recognized area 101-1) due to an effect of noise or the like. In FIG. 19(a), in order to enhance visibility, the erroneously recognized area 99-1 and the normally recognized area 101-1 are illustrated while they can be discriminated from each other. However, when they are displayed on an actual display device, the erroneously recognized area 99-1 and the normally recognized area 101-1 are not displayed with being differentiated from each other.

FIG. 19(b) is a diagram showing a screen 305 when the display method is changed in accordance with the identification probability value (identification degree) according to the method of this embodiment. For example, the screen 305 displays an area having a low identification probability (erroneously recognized area 99-2) while increasing the transparency thereof, and thus the area is displayed with being differentiated from a normally recognized area (normally recognized area 101-2). In FIG. 19(b), when they are displayed on an actual display device, the erroneously recognized area 99-1 and the normally recognized area 101-1 are displayed with being differentiated from each other.

Figure 20:
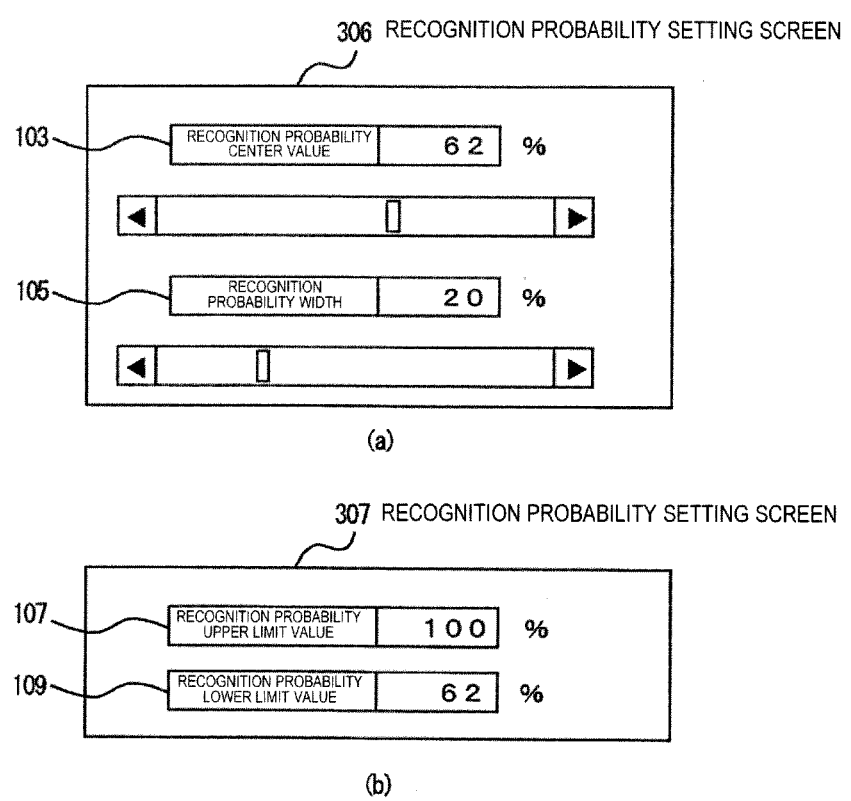
[FIG. 20] is a diagram showing a recognition probability setting screen.
Figure 21:
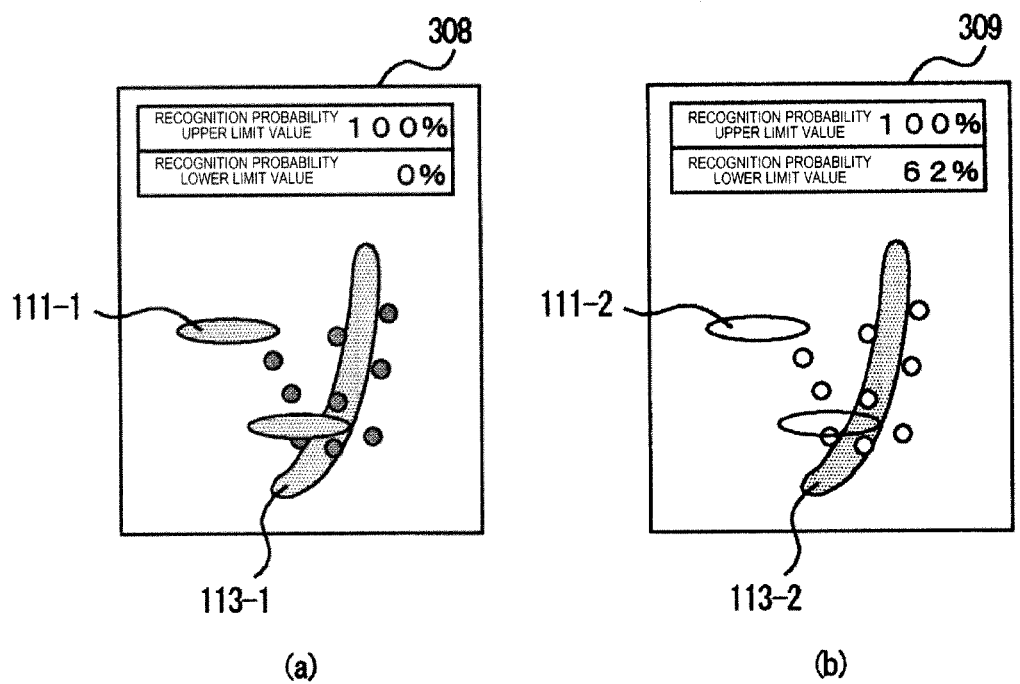
[FIG. 21] is a diagram showing a display screen of recognition probability and a recognition result.

FIGS. 20 and 21 show screens for setting the range of the identification probability value by the operator.

On the identification probability map 97 (FIG. 16) calculated in step 2004, a value from "0" to "255" is set as an identification probability value at each coordinate. However, in order to enable the operator to set the identification probability value intuitively, the identification probability value "0" on the identification probability map 97 is displayed as the recognition probability "0%" in FIGS. 20 and 21, and the identification probability value 255" is displayed as the recognition probability "100".

FIG. 20(a) shows a recognition probability setting screen 306 to which the operator can input a recognition probability center value 103 and a recognition probability width 105. The operator may directly input the recognition probability value from the keyboard 17 to the recognition probability setting screen 306, or input the recognition probability value by operating a bar through the mouse 15.

FIG. 20(b) shows a recognition probability setting screen 307 to which the operator can input a recognition probability upper limit value 107 and a recognition probability lower limit value 109.

FIG. 21(a) shows a screen 308 on which a biomedical tissue of the examinee 33 is displayed when the recognition probability upper limit value "100%" and the recognition probability lower limit "0%" are set in the recognition probability setting screen 307. On the screen 308, all recognized tissues containing a low recognized area 111-1 and a high recognized area 113-1 are displayed with the same expression (brightness, color saturation, transparency, etc.) irrespective of the recognition probability.

FIG. 21(b) is a screen 309 on which a biomedical tissue of the examinee 33 is displayed when the recognition probability upper limit value "100%" and the recognition probability lower limit value "62%" are set in the recognition probability setting screen 307. The screen 309 displays a low recognized area 111-2 out of the recognition probability range while the transparency of the low recognized area 111-2 is increased, and also displays a high recognized area 113-2 in the recognition probability range with the same expression irrespective of the recognition probability or displays it in accordance with the recognition probability.

(3-11. Effect of Display Setting of Screen)

As described above, the expression method of the biomedical tissue display can be changed by specifying the recognition probability, and thus the operator can display the tissue-of-interest while emphasizing the tissue-of-interest in accordance with operator's fancy. Accordingly, the operator can accurately diagnose the biomedical tissue, so that erroneous diagnosis caused by erroneous recognition of the biomedical tissue can be reduced.

(4. Other)

The medical image information based on the multi-energy imaging may be displayed by properly combining the discrimination of the display method based on the type of the biomedical tissue, the display method based on the identification degree of the biomedical tissue and the display method based on the operator's recognition probability setting. By displaying the medical image information from different perspectives, the diagnosis of the biomedical tissue can be speeded up, and thus more accurate diagnosis can be performed.

In the above-described embodiment, the X-ray CT image has been described. However, the present invention may be applied to diagnosis of medical image information acquired by a medical imaging apparatus such as an X-ray fluoroscopic imaging apparatus, an MRI apparatus, an ultrasonic diagnosis apparatus or the like.

The preferred embodiment of the medical image processing apparatus according to the present invention has been described, however, the present invention is not limited to this example. It is apparent that a person skilled in the art can conceive various modifications or alterations in the scope of the technical ideal disclosed in this application, and it is understood that they also belong to the technical scope of the present invention.

Description of Reference Numerals

1 Medical Image Processing Device, 3 CPU, 5 main memory, 7 storage device, 9 display memory, 11 display device, 13 controller, 15 mouse, 17 keyboard, 19 network adaptor, 21 system bus, 23 medical imaging apparatus, 25 image data base, 27 network, 29 gantry, 31 X-ray source, 33 examinee, 35 table, 37 irradiation X-ray, 39 X-ray detector, X-ray controller, 43 gantry controller, 45 table controller, 47 data collecting circuit, 49 reconstruction calculator, 51-1, 51-2 tissue name, 53-1, 53-2 display color, 55-1, 55-2, 61-1, 61-2 tube voltage, 57-1, 57-2, 63-1, 63-2, 75, 77-1 to 77-5 average CT value, 59-1, 59-2, 65-1, 65-2 standard deviation, 67 "OK" button, 69 "cancel" button, 71 CT value (tube voltage 80 kV), 73 CT value (tube voltage 140 kV), 79-1 to 79-3 probability distribution data of tissue, 81 identification map, 83-1 to 83-5 coordinate, 85 identification boundary, 87 distance map, 89 maximum probability map, 91 center value, 93 coordinate-of-interest, 95 boundary, 97 identification probability map, 99-1, 99-2 erroneously recognized area, 101-1, 101-2 normally recognized area, 103 recognition probability center value, 105 recognition probability width, 107 recognition probability upper limit value, 109 recognition probability lower limit value, 111-1, 111-2 low recognition probability area, 113-1, 113-2 high recognition probability area, 301 to 309 screen.

The invention claimed is:

1. A medical image processing device for making a display device display medical image information based on two or more different energy intensities obtained by irradiating an examinee with X-ray, characterized by comprising:
   statistic amount information acquiring means for acquiring statistic amount information corresponding to a type of a biomedical tissue of the examinee, for each energy intensity amongst the two or more different energy intensities;
   identification map creating means for creating an identification map for identifying the type of the biomedical tissue, on the basis of the statistic amount information, the identification map including areas corresponding to respective biomedical tissues;
   tissue identifying means for identifying the type of the biomedical tissue in the acquired medical image information on the basis of the identification map;
   identification probability map creating means that sets an identification probability value of the biomedical tissue on the basis of an existence probability value of the biomedical tissue and distance from a boundary of the type of the biomedical tissue to each point on the identification map, for each particular area on the identification map associated with a corresponding biomedical tissue, thereby creating an identification probability map representing an identification degree of the biomedical tissue; and
   display means for making the display device display an identification result of the tissue identifying means as the medical image information on the basis of the identification degree.

2. The medical image processing device according to claim 1, wherein the identification map creating means selects the type of a specific biomedical tissue having a highest existence probability value, for each area, corresponding to a combination of statistic amount information of two or more different energy intensities to create an identification map.

3. The medical image processing device according to claim 2, wherein an identifier for identifying the selected type of the specific biomedical tissue is set in the identification map, for each area.

4. The medical image processing device according to claim 3, wherein the display means displays the type of the specific biomedical tissue identified by the tissue identifying means while setting a color different for each type of the biomedical tissue.

5. The medical image processing device according to claim 1, wherein the display means displays the type of the biomedical tissue identified by the tissue identifying means while setting a color different for each type of the biomedical tissue and further setting a gradation corresponding to the identification probability value of the biomedical tissue of each area which is determined by the tissue identifying means.

6. A medical image processing method for a medical image processing device for making a display device display medical image information based on two or more different energy intensities acquired by irradiating an examinee with X-ray, characterized by comprising:
   a statistic amount information acquiring step for acquiring statistic amount information corresponding to a type of a biomedical tissue of the examinee, for each energy intensity amongst the two or more different energy intensities;
   an identification map creating step for creating an identification map for identifying the type of the biomedical tissue on the basis of the statistic amount information, the identification map including areas corresponding to respective biomedical tissues;
   a tissue identifying step for identifying the type of the biomedical tissue in the acquired medical image information on the basis of the identification map;
   identification probability map creating step for setting an identification probability value of the biomedical tissue on the basis of an existence probability value of the biomedical tissue and distance from a boundary of the of the biomedical tissue to each point on the identification map, for each particular area on the identification map associated with a corresponding biomedical tissue, thereby creating an identification probability map representing an identification degree of the biomedical tissue; and
   a display step for making the display device display an identification result of the tissue identifying step as the medical image information on the basis of the identification degree.

7. A program of instructions embodied in a non-transitory computer-readable medium and executable by a computer to make the computer function as a medical image processing device comprising:
   statistic amount information acquiring means for acquiring statistic amount information corresponding to a type of a biomedical tissue of the examinee, for each energy intensity amongst the two or different energy intensities;
   identification map creating means for creating an identification map for identifying the type of the biomedical tissue, on the basis of the statistic amount information, the identification map including areas corresponding to respective biomedical tissues;
   tissue identifying means for identifying the type of the biomedical tissue in the acquired medical image information on the basis of the identification map;
   identification probability map creating means that sets an identification probability value of the biomedical tissue on the basis of an existence probability value of the biomedical tissue and distance from a boundary of the type of the biomedical tissue to each point on the iden-
tification map, for each particular area on the identification map associated with a corresponding biomedical tissue, thereby creating an identification probability map representing an identification degree of the biomedical tissue; and display means for making the display device display an identification result of the tissue identifying means as the medical image information on the basis of the identification degree.

8. A multi-energy type X-ray CT apparatus for acquiring transmitted X-ray information when an examinee is irradiated with X-rays having two or more different energy intensities and making medical image information by using the acquired X-ray information, characterized by comprising:

statistic amount information acquiring means for acquiring statistic amount information corresponding to a type of a biomedical tissue of the examinee, for each energy intensity amongst the two or more different energy intensities;

identification map creating means for creating an identification map for identifying the type of the biomedical tissue, on the basis of the statistic amount information, the identification map including areas corresponding to respective biomedical tissues;

tissue identifying means for identifying the type of the biomedical tissue in the acquired medical image information on the basis of the identification map;

identification probability map creating means that sets an identification probability value of the biomedical tissue on the basis of an existence probability value of the biomedical tissue and distance from a boundary of the type of the biomedical tissue to each point on the identification map, for each particular area on the identification map associated with a corresponding biomedical tissue, thereby creating an identification probability map representing an identification degree of the biomedical tissue; and display means for making the display device display an identification result of the tissue identifying means as the medical image information on the basis of the identification degree.

* * * * *